(12) United States Patent
Heidrich et al.

(10) Patent No.: US 9,846,060 B2
(45) Date of Patent: Dec. 19, 2017

(54) OPTICAL SENSOR ARRANGEMENT AND METHOD FOR MEASURING AN OBSERVABLE

(71) Applicant: Fraunhofer-Gesellschaft zur Foerderung der Angewandten Forschung e.V., Munich (DE)

(72) Inventors: Helmut Heidrich, Berlin (DE); Peter Lützow, Berlin (DE); Daniel Pergande, Berlin (DE)

(73) Assignee: Frauhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 14/780,552

(22) PCT Filed: Mar. 28, 2013

(86) PCT No.: PCT/EP2013/056715
§ 371 (c)(1),
(2) Date: Sep. 27, 2015

(87) PCT Pub. No.: WO2014/154283
PCT Pub. Date: Oct. 2, 2014

(65) Prior Publication Data
US 2016/0047677 A1    Feb. 18, 2016

(51) Int. Cl.
*G02B 6/293* (2006.01)
*G01D 5/26* (2006.01)
(Continued)

(52) U.S. Cl.
CPC ......... *G01D 5/266* (2013.01); *G01N 21/7746* (2013.01); *G02B 6/29343* (2013.01); *G02B 6/12007* (2013.01)

(58) Field of Classification Search
CPC ............ G01N 21/7746; G02B 6/29338; G02B 6/29343
(Continued)

(56) References Cited

U.S. PATENT DOCUMENTS

| 7,796,262 B1 * | 9/2010 | Wang ................. G01N 21/7746 356/436 |
| 9,170,371 B2 * | 10/2015 | Santori ............. G01N 21/7746 |
| 2012/0182552 A1 | 7/2012 | Heidrich et al. |

FOREIGN PATENT DOCUMENTS

| EP | 2267432 A1 | 12/2010 |
| EP | 2515099 A1 | 10/2012 |

OTHER PUBLICATIONS

International Preliminary Report on Patentability issued in PCT/EP2013/056715, dated Sep. 29, 2015, 11 pages.
(Continued)

*Primary Examiner* — Jonathan Hansen
(74) *Attorney, Agent, or Firm* — Faegre Baker Daniels LLP (57) ABSTRACT

An optical sensor arrangement for measuring an observable, the arrangement including an optical resonance circuit including at least a first and a second optical resonator, each of the optical resonators including an entry port for coupling light into the optical resonator and a drop port for decoupling light from the optical resonator. The first and second resonator are configured such that only a portion of the first and second resonator detects the presence of the observable, a size of the portion of the first resonator being different from a size of the portion of the second resonator. The optical resonance circuit further configured to be coupled to a light generation circuit and to a detector unit for detecting light.

16 Claims, 4 Drawing Sheets

(51) Int. Cl.
*G01N 21/77* (2006.01)
*G02B 6/12* (2006.01)

(58) Field of Classification Search
USPC ......................................................... 356/480
See application file for complete search history.

(56) References Cited

OTHER PUBLICATIONS

International Search Report and Written Opinion issued in PCT/EP2013/056715, dated Jan. 9, 2014, 16 pages.
Yi, Huaxiang. "Dual-Microring-Resonator Interference Sensor." Applied Physics Letters, 95:191112-1-191112-3, 2009.
Zhou, Zhiping, et. al. "Silicon Microoring Sensors." Proc. of SPIE, 8236:823617-1-823617-10, Feb. 9, 2012.

* cited by examiner

Fig. 5

OPTICAL SENSOR ARRANGEMENT AND METHOD FOR MEASURING AN OBSERVABLE

CROSS-REFERENCE TO RELATED APPLICATION

This application is a national phase application of PCT Application No. PCT/EP2013/056715, internationally filed Mar. 28, 2013, which is herein incorporated by reference in its entirety.

TECHNICAL FIELD

This disclosure relates to an optical sensor arrangement for measuring an observable, the arrangement including an optical resonance circuit.

BACKGROUND

Optical sensor arrangements are used for measuring at least one observable, where the observable can be the presence of a specific substance or other physical properties, such as changes in pressure or temperature. Some optical sensor arrangements include optical resonance circuits, which include at least one optical resonator, such as an optical microring resonator, as a very sensitive optical sensor type for sensing the observable. In many cases the resonator is exposed to a medium such as a gas or a liquid, where the medium may carry a chemical compound, a biological substance, or the like, to be measured by the optical sensor arrangement. In several cases the optical resonator is covered by a covering material (or active layer) which includes an active material such that molecules of the substance to be detected can dock at the active material.

Optical resonators have the property of allowing light of a specific frequency that represents a resonance frequency of the optical resonator (i.e., the wavelength of the light multiplied by an integer corresponds to the effective refractive index multiplied by the length of the resonator) to enter the optical resonator while light of other wavelengths does not enter the resonator.

Many optical resonators have the property that when a physical condition, such as temperature or pressure, of the surrounding medium changes or a substance, such as a chemical or biological compound or substance, attaches to at least one of the surfaces of the resonator, the optical length of the optical resonator changes with it, i.e., the resonance frequency of the optical resonator is shifted. The shift in resonance frequency or optical length can be used to determine whether the observable to be sensed has changed or is found in the medium.

A problem to be solved is to design an optical sensor arrangement for measuring an observable and provide an alternative solution to the optical sensor arrangements found in the prior art.

SUMMARY

In embodiments of the disclosure, an optical sensor arrangement for measuring at least one observable includes an optical resonance circuit including at least a first and a second optical resonator, each of the optical resonators including an entry port for coupling light into the optical resonator. Furthermore, according to the disclosure the optical resonance circuit also includes a drop port for decoupling light from the optical resonator, which can be different from the entry port. In the sense of this application, an entry port or a drop port is defined as a neighborhood between an optical path, such as a waveguide, and an optical resonator, such as a microring resonator, in which light traveling within either the waveguide or the optical resonator can enter the other through the evanescent field of the light component.

The optical resonators each have an optical length which is variable depending on the at least one observable. To increase the range (or sensitivity) of the sensor, a size of a portion of the first optical resonator which is exposable to the observable is different from a size of a portion of the second optical resonator.

The range or sensitivity of a resonator is connected to its free spectral range, FSR, which describes the interval between two subsequent resonance peaks in the transmission spectrum of a resonator. Each resonator does not only have a single resonance frequency, but several resonance frequencies (which may be attributed to the resonant condition m $\lambda$=n_eff L, where m is a natural integer, $\lambda$ is the wavelength of the incident light, n_eff is the effective refractive index and L the length of the resonator at subsequent m's). The free spectral range, FSR, is the interval between two subsequent resonance frequencies, e.g. m=1 and m=2. When an optical resonator is exposed to the observable, the effective refractive index changes and, thus the resonance frequency of the resonator is shifted accordingly. The difference between the resonance frequency in a base state of the resonator, i.e. when the resonator is not exposed to the observable, and an active state of the resonator, i.e. when the portion of the first or second resonator is exposed to the observable, is used as an indicator of the presence of the observable and may be used as a quantitative measurement of the presence of the observable. Often a (linear) relationship exists between the quantity of the observable and the shift in the resonance frequency from the base to the active state of the resonator. However, when the difference of the resonance frequency of the resonator in its base and active state is about the size of the FSR, the resonator is said to be saturated, because the presence of the observable may be missed, misinterpreted or miscalculated.

By configuring the first and second resonator such that different sized portions of the first and second resonators are usable for the detection of an observable, the shift of the resonance frequencies of the first and second resonators differs as well, since less exposure to the observable effects a smaller resonance shift than an increased exposure to the observable. When the size of the portions of the first and second resonators differ, and under the assumption that the concentration of the observable is about equal for the first and second resonator, the shifts in resonance frequency also differ.

The difference in resonance frequency shifts increases the range over which the presence of an observable can be detected. For example, if a large portion of the first resonator is configured to detect the observable (e.g. by covering said portion with an active layer), many particles or quantities of the observable can be retained at the portion and these particles induce a large resonance frequency shift between the base and active state of the first resonator. If the portion configured for the detection of the observable of the second resonator is, e.g. half the size of the portion of large portion of the first resonator (with the resonators moving an about equal length in this example), then the shift in resonance frequencies of the second resonator will only be a fraction of the shift in resonance frequencies of the first resonator, e.g. half the shift compared to the shift of the first resonator in case of a linear relationship between the presence of the observable and the shift. This relationship holds when the exposed portions only differ in size. In further embodiments the respective portions of the first and second resonators may be covered by an active layer for the accretion of the observable, wherein the concentration of the active material of the active layer (i.e. the number of places to which the observable to be detected may dock per area) is constant. In other embodiments, the concentration of the active material may also differ, though.

Even though the range extension so far has been explained by referring to different portions of the first and second resonators being exposed to the observable, the range of the optical sensor arrangement can, in alternative embodiments, also be extended by covering an identical portion of the first and second resonators by an active layer, where the concentration of active material of the active layer of the first and second resonators differ, i.e. the number of places to which the observable may dock per area is different for the first and second resonators. Doubling the concentration between the first and second resonators is equivalent to doubling the shift of resonance frequencies from the base to the active state of the respective resonator.

Both embodiments (differing size and differing concentration) may be combined to extend the range of the sensor arrangement. Both the concentration of the active material and the size of the portion to which the active material may be applied can be different the same time.

By using more than two resonators the range of the measurement can be extended even further. Some resonators may have a small sensitivity to the observable, while other resonators are very sensitive to the observable, but may saturate much faster.

In some embodiments, the FSR of the first and second resonator is substantially the same in their base state, either by construction or by tuning one of the resonator's FSR through a control field.

The portion of the first and second resonators which is exposable to the observable may be a portion of one or more surfaces of a microring resonator for example, or a surface of a Fabry-Perot interferometer. The exposed portion of the first and second resonators is preferentially smaller than the entire surface but bigger than zero. Similarly, when the first and second resonators include an active layer, the concentration of the active material in the active layer is bigger than zero.

An optical resonance circuit can include more than 10 or 50 resonators, and the different resonators can be configured to have differing sensitivities.

In some embodiments, the optical resonance circuit may optionally be configured to couple to a light generation circuit or a detector unit.

In some embodiments, the optical resonance circuit includes interfaces for coupling a light generation circuit, a detector unit or a control unit to the optical resonance circuit. By modularizing the optical sensor arrangement, the optical resonance circuit may be constructed as a disposable resonance circuit, which is disposed of after a single measurement or a fixed number of measurements. The resonators of the optical resonance circuit may be placed on a substrate, which can be mounted on a casing. The substrate or casing has a predefined shape and can be mounted into an optical resonance circuit mounting interface of the optical sensor arrangement. Once the disposable optical resonance circuit is placed in the optical sensor arrangement, and the light generation circuit, detector unit and control unit are connected to the interfaces, the measurement of the observable can commence. After the measurement, the optical resonance circuit is removed from the arrangement including the light generation circuit, detector unit and/or control unit.

In some embodiments, the optical resonance circuit includes further resonators. At least one of the further resonators is configured as a gauge resonator, which is not exposed to the observable. For example, the gauge resonator may be fully encapsulated from the environment.

In some embodiments, the exposed portion of the resonator is free of an encapsulating material, whereas the remainder of the resonator is covered by the encapsulating material. The portion covered by the encapsulating material is, thus, not configured to detect the observable and cannot effect a resonance frequency shift.

Additionally, the optical resonance circuit is configured to be coupled to a light generation circuit, which preferably includes a light source such as a laser. The light generation circuit may be coupled to an interface of the optical resonance circuit, which feeds light from the interface to the entry ports of the first and second resonators. The interface may include an optical coupler for transferring light from the light generation circuit to the optical resonance circuit. In other embodiments the light generation circuit is part of the optical sensor arrangement and may not be detachable from the optical resonance circuit.

Furthermore, the arrangement is configured to be coupled to a detector unit for detecting the light including at least one photosensitive element. The detector unit may be optically coupled to the drop port of each of the at least two optical resonators. Hence, light emitted from the light generation circuit travels along an optical path and passes the entry ports of each of the at least two optical resonators, and only when the light has a frequency corresponding to one of the resonance frequencies of the at least two optical resonators, enters and exits the resonator through the drop port and travels into the detector unit. By coupling the detector unit to the drop ports of the optical resonators, the detector unit detects an intensity maximum at optical resonance frequencies of the at least two optical resonators. Since the detector unit only receives a signal when a resonance criterion is met, i.e., light passes through at least one of the optical resonators and exits at the drop port to be detected at the detector unit, the detector only receives relevant data. In other embodiments, the detector is coupled to the entry ports and, thus, only receives data which is not relevant and has to determine the resonance frequencies from an intensity minimum (i.e., from data not received), the accuracy of the measurement can be improved or the complexity of the data analysis can be simplified. The optical resonance circuit may include an interface or several interfaces for coupling light from the optical resonators to the detector unit. These interfaces may be optical couplers for example. In other embodiments the detector unit is part of the optical sensor arrangement and may not be detachable from the optical resonance circuit.

The optical sensor arrangement may also include a control unit for selectively modulating the first optical length, the second optical length, an amplitude of the first light component or an amplitude of the second light component. Since the optical sensor arrangement includes several optical resonators, it is of interest to separate the signals from the first and second optical resonators. By specifically modulating either the optical lengths of the first and second optical resonators by a time-dependent signal specific to an optical resonator, the signal received at the detector unit also includes said time dependence and thus allows to determine whether the detected signal originates from the first or second optical resonator. If the first and second optical resonators are modulated with different time dependencies, it can be easily determined which signal received at the detector corresponds to which optical resonator.

The control unit may be part of the optical sensor arrangement or may be coupled to the optical resonance circuit via signal interfaces. While the modulators or switches can be part of the optical sensor arrangement, the signal of how the resonators or the optical paths leading to or from the resonators are modulated or switched, respectively, is delivered by the control unit. These signals can be fed from the control unit to the modulators or switches of the optical resonance circuit via a signaling interface. The interface forwards the signals to the modulators and effects the modulation or the switching, respectively. In case the optical lengths of the resonators differ from each other, the control unit can also be used to bias the optical length of some of the resonators so that their optical length coincides with the optical length of a reference optical resonator (which may be resonator of the circuit or an optical resonator with a preset optical length).

Supposing that a first light component of light emitted from the light generation circuit is of a resonance frequency specific to the first optical resonator and a second light component of said emitted light is of a resonance frequency specific to the second optical resonator, modulating the amplitudes of the first and second light components in a resonator-specific manner also allows to determine whether a signal received at the detector unit originates from the first optical resonator or the second optical resonator. Depending on the chosen architecture of the optical sensor arrangement, also the lengths of the optical paths to and from the optical resonance circuits may be altered individually for each optical resonator in order to identify signals received at the detector unit as originating from the first or second optical resonators or their corresponding paths.

The amplitude of the first and second light components can be modulated, and it is also within the scope of this application that the modulation is such that the amplitude equals zero, i.e., the control unit for modulating the amplitudes of the light components is a switch which may switch on and off with a specific time variance. Again, signals arriving at the detector unit can be identified as originating from the first or second optical resonator or the paths to and from the optical resonance circuit based on the switching frequency.

In a base state of the first and second optical resonators, said optical resonators may have an identical or different optical length. A base state in the sense of this application is understood as the state in which the resonators are not exposed to the observables to be detected.

In an active state, i.e., a state in which the optical sensor arrangement is exposed to a medium or gas which may include the observables to be detected, the observable, such as a change in temperature, a change in pressure, or a specific biological or chemical compound or substance in the medium, affects the optical resonators and causes a change in the effective refractive index and thus a change in their optical length, thereby changing the resonance frequencies. In other words, the shift in resonance frequencies from the base state to the active state, in which a substance to be detected is part of the medium, has the effect that light of, for example, the first component which passes the first optical resonator in a base state no longer passes said optical resonator in its active state. Be detuning the frequency of the first light component, the active state of the resonance frequency of the first optical resonator can be determined, and a signal received at the detector unit can again be identified by the modulation frequency imposed by the control unit.

Even though detuning the light source is a method for determining the frequency shifts, the presence of a substance can also be identified by tuning the first and second optical resonators in their base state such that a signal is received at the detector unit. Each signal is modulated by a specific frequency identifying the light as having passed through the first or second optical resonator. If one of the signals now disappears, it can also be assumed that the presence of an observable has been detected.

It is also sufficient to only modulate one of the optical resonators or the paths leading to the optical resonators, since one of the first and second optical resonators can be assumed to be modulated with a modulation frequency of zero.

In some embodiments as mentioned, the optical lengths of the first and second optical resonators may be different in a base state. It is very difficult to build optical resonators which have the exact same resonance frequencies. Hence, it is easier to construct the optical sensor arrangement by not imposing the restriction that the resonance frequency of the first and second optical resonators is identical. If said optical lengths are different in a base state, the first and second light components can be interpreted to be light of a first and second frequency, respectively. The first component having the first frequency corresponds to a resonance frequency of the first optical resonator, and the second light component having a second frequency corresponds to the resonance frequency of the second optical resonator.

In some embodiments the first and second optical lengths of the first and second optical resonators when in an active state are different.

In order to simplify the arrangement, a light generation circuit may include a tunable light source for generating light of different frequencies. In some embodiments an interval of frequencies can be scanned by the light source periodically, and thus, at a specific time, light of a first frequency, i.e., the first light component, and, at a later time, light of a second frequency, i.e., the second light component, is generated.

In some embodiments, the light generation is coupled to the first and second optical resonators by a single optical waveguide. Embodiments allow for a simple construction. However, said construction makes it more difficult to individually modulate the amplitude of the first or second light component. A device for modulating the amplitude can be placed in the optical waveguide between the first and second optical resonators, i.e., light arriving at the first optical resonator has a first amplitude, and said amplitude is reduced or in specific examples enhanced and now passes by the second optical resonator.

In contrast, the first optical resonator may be coupled to the light generation circuit by a first optical waveguide, and the second optical resonator may be coupled to the light generation circuit by a second optical waveguide. Each waveguide may be coupled to its own light source, or a single light source may be used, the light of which is split by a beam splitter or an optical coupler. Using an optical path for each of the first and second optical resonators allows to individually modulate optical lengths of the first and second optical paths in some embodiments. Furthermore, a device for modulating the amplitude may be placed in each optical path. This allows to individually modulate the amplitude of the light component in each optical path by a different time dependence. A modulator can, for example, be a waveguideintegrated PIN diode used as an electro-optical modulator, a Mach-Zehnder based modulator, an electro-optical amplitude modulator, a light chopper, a mode filter or similar devices.

In some embodiments, the detector unit is coupled to the first and second optical resonators by a single optical waveguide. This again allows for a simple construction of the arrangement. The optical waveguide passes each drop port of the first and second optical resonators and allows light exiting at said drop ports to be detected at the detector unit.

In contrast, the first optical resonator may be coupled to the detector unit by a third optical waveguide, and the second optical resonator may be coupled to the detector unit by a fourth optical waveguide. This case is similar to the case where the light generation circuit couples to the first and second optical resonators through an individual optical path. In particular, it is possible to modulate light after said light has passed through the first or second optical resonator. This may be advantageous since light passing through the optical resonators need not be modulated beforehand and the intensity of the signal may be improved. The third and fourth optical waveguides may be coupled by an optical coupler situated between the optical resonance circuit and the detector unit, allowing the use of a smaller detector unit.

The waveguides leading to and from the optical resonance circuit may be coupled to corresponding waveguides of the optical resonance circuit via interfaces such as optical couplers. These optical complex may be part of the optical resonance circuit or another circuit of the optical sensor arrangement.

An alternative to using a coupler coupling the third and fourth optical waveguides (or further waveguides) is using a camera, several photo detector units or a single photo detector unit with a photosensitive area large enough to accommodate all light beams emitted from the third, fourth and further waveguides. Using a camera, which may include a lens system, has the advantage that the signals received by the camera from the different waveguides may be detected by different pixels of the photosensitive chip (f.e. a CMOS or a CCD, wherein the plurality of pixels corresponds to a plurality of photosensitive elements of the detector unit) of the camera. A control unit of the camera can successfully separate the signals due to their local distribution on the chip, identifying which signal is received from which optical resonator. Using a camera can have the further advantage that a control unit for selectively modulating the first or second optical length or the amplitude of the first or second light component is not necessary, since the local distribution allows a separation of signals. However, the camera can also be an additional means to confirm that the signals separated by a, f.e., lock-in amplifier are indeed from a particular resonator. A camera, particularly for detecting wavelengths used in telecommunications, f.e. 1.5 µm, can be quite costly though. Using several photo sensitive elements, each coupled to one of the third, fourth or further waveguides also results in a separation of signals without the need for a control unit for selectively modulating the first or second optical length or the amplitude of the first or second light component. However using several photosensitive elements may be more costly and require a bigger substrate for mounting the optical sensor arrangement on a single substrate.

Even though the optical sensor arrangement described so far only comprises a first and a second optical resonator, further optical resonators may be employed. Said resonators may each have their own individual optical waveguide from the light generation or to the detector unit or may share an optical path with another optical resonator. It is also possible to connect a few optical resonators by a single optical waveguide while further optical resonators each have their own optical path.

When more than two optical resonators are used, each resonator can be configured to detect the at least one observable, each resonator having a different sensitivity. Each optical resonator can be constructed such that it has a different optical length in its base state from the other resonators. Consequently, the light generation circuit (besides the first and second light component) should emit further components, each further component matching a resonance frequency or optical length of one of the further optical resonators. In case an interval of frequencies is scanned, the further light components may be scanned at different times than the first and second light components.

Microring resonators can be used as optical resonators. However, other types of resonators may be employed, such as Fabry-Perot resonators or photonic crystal resonators.

In some embodiments the optical sensor arrangement includes a laser in the light generation circuit, where the laser is tunable. Further lasers may be employed. In particular, a distributed feedback (DFB) laser may be used. The laser can be tunable.

In order to ensure that the first and second optical resonators are specific to the chosen observable, each resonator may comprise an active layer for the selective accretion of one or more substances to be detected. The active layer may be exclusively specific to molecules or a group of specific substances. For example, the active material may exploit the key-lock principle to bind specific antibodies, DNA or other oligo-nucleotides. The active layer or covering material can be a polymer film which is coated onto the optical resonators. It can also include a solution which is applied to the portion of the resonators which can be contacted by the observable (substance or compound of substances to be detected). The application of the active layer can be performed similarly to the techniques known from spotted or oligo-nucleotide microarrays, when the optical resonance circuit is used as a (bio)lab-on-a-chip. However, different techniques can be used to apply an active layer on the resonators. When spotting the resonators the active material may be a antibody specific to the observable to be detected. When spotting the resonators, the active material may be specific and selective to the observable to be detected exclusively, or may be selective to several substances with an equal specificity or may have a higher selectivity for a first substance (primary specificity) and lower specificities for other substances (secondary specificity). The overall specificity of the sensor arrangement can be improved by the application of a set of different active materials, each material applied to a different resonator and having a different primary specificity in some embodiments. By selecting different materials the effects of the secondary specificities can be reduced the primary specificities enhanced due to the extended range of the sensor arrangement. This may be helpful for example in case a defined biomolecule or germ has to be identified from a diverse mixture of biomolecules/germs to which the active material has secondary specificities also.

The optical sensor arrangement may further include an amplifier as part of the detector unit, preferably a differential amplifier for evaluating output signals of the at least one light-sensitive element. To separate the signals, a lock-in amplifier may be used. The signal of the first sensitive element may be filtered by a signal of the modulation frequency for each optical resonator. Due to a periodicity of the modulation signal, the different components which are not modulated by the modulation frequencies can be eliminated, and only the signal corresponding to a specific optical resonator or its corresponding optical path is separated.

Further, a second (or, as previously mentioned, an alternative) detector unit can be used with the optical sensor arrangement. The detector unit may be situated at an entry side of the first and second optical resonators, which is the side where the entry ports of said resonators are situated. In contrast to the first detector unit, the second detector unit then does not measure a transmission spectrum of the optical resonators, but an absorption spectrum. The absorption spectrum lacks intensities in frequencies, where the first or second optical resonators are resonant. The second detector unit can be used to verify results of the first detector unit or serve as a redundant detector unit used when the first detector unit fails.

Further details regarding optical sensor arrangements are found in the following description of embodiments and the drawings illustrating various aspects of the embodiments. It is pointed out that features not claimed in the independent or dependent claims but shown in the drawings and described in the corresponding description are, each in its own right, also features of this application. They may be claimed without necessarily including all features shown or described in the embodiments. Consequently, any single feature shown in embodiments may be claimed individually. In particular, features described in connection with the optical sensor arrangement may be claimed for the disclosed method and vice versa.

While multiple embodiments are disclosed, still other embodiments of the disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

Embodiments of this disclosure are subsequently explained with reference to FIGS. 1-4.

FIG. 1b illustrates the increase in sensitivity over a greater range due to the resonator array, according to embodiments of the disclosure;

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1A:
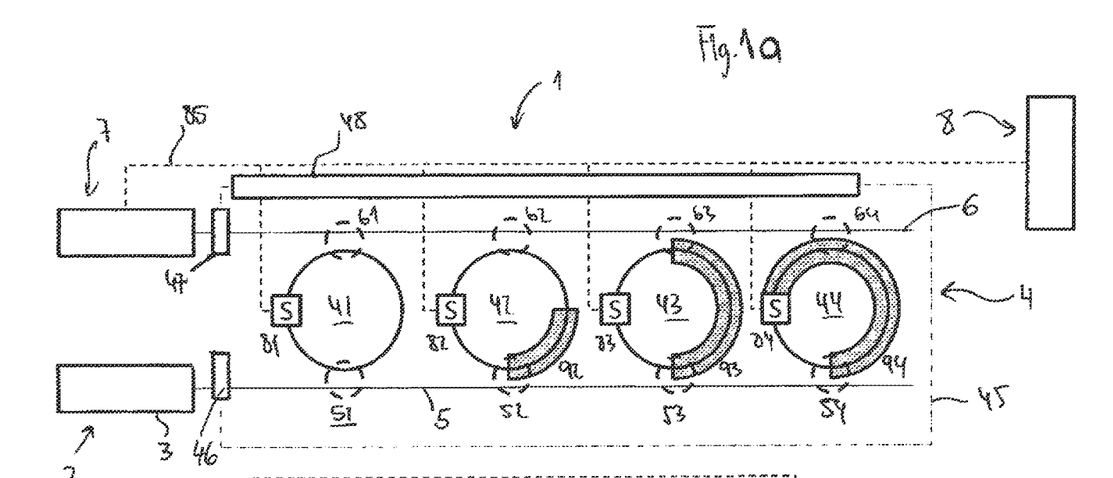
FIG. 1a represents an optical sensor arrangement, according to embodiments of the disclosure.

FIG. 1 discloses an optical sensor arrangement 1 including a light generation circuit 2 which includes a DFB laser 3. Furthermore the arrangement 1 includes an optical resonance circuit 4 which is optically coupled to the light generation circuit 2 by a single optical waveguide 5. The arrangement further includes a single optical waveguide 6 which connects the optical resonance circuit 4 to a detector unit 7. The arrangement further includes a control unit 8 for modulating the optical lengths of the optical resonators of the optical resonance circuit. Optionally, a further, second, detector unit can be placed along waveguide 5 at the side opposite light generation circuit 2.

The DFB laser 3 is tunable, i.e., can scan through an interval of frequencies where the interval of frequencies is chosen such that at least one resonance frequency of each of the optical resonators of the optical resonance circuit is emitted during the interval. The optical resonance circuit 4 shown in FIG. 1 includes four different optical microring resonators 41-44. In some embodiments, the optical lengths in a base state of the arrangement 1 are different, but can be tuned to be identical in their base state by the application of an electrical field through the control unit. However, it is also possible to use optical resonators 41-44 which have identical optical lengths in a base state. Furthermore several, but not all, optical resonators may have the same wavelength while others have different wavelengths.

The optical resonators 41-44 are optically coupled to the single optical waveguide 5 through entry ports 51-54. The entry ports are defined by a region in which the single optical waveguide and parts of each of the optical resonators 41-44 are situated so closely next to each other that an evanescent field of light traveling through the single optical waveguide may couple to the optical resonators. Each of the optical resonators 41-44 in addition to an entry port has a drop port 61-64 which optically couples the optical resonators to the single optical waveguide 6. The drop port is a region in which the optical waveguide is so close to the optical resonator that the evanescent field of a constructively interfering light wave traveling inside the optical resonator may couple into the single optical waveguide. Light traveling through the single optical waveguide 6 is then directed to a detector unit 7 which includes at least one photosensitive element. The light generation circuit 2, the optical resonance circuit 4, as well as the optical waveguides and the detector unit may be arranged on a single semiconductor substrate such as a silicon substrate. However, the different components of the arrangement, for example the light generation circuit and the optical resonance circuit, may also be arranged on separate substrates and only be coupled by the optical waveguides.

The control unit 8 includes a CPU or a microcontroller or a field programmable gate array and is connected to a modulation device 81-84 where each of the modulation devices is configured to modulate the optical length of the corresponding optical resonator. The control unit 8 may include several wave generation circuits for imposing a modulation on the optical length of the optical resonators. The devices 81-84 for modulating the optical length of the resonator can be heating elements, such as heating wires or heating layers for rapid setting and adjusting the temperatures of the resonators, or electrical contacts for applying an electrical field to the respective resonator. Both, changes in temperature or in the electric field, may change the effective refractive index and can be used for modulating the optical length. As long as a heating element or electrical contacts are, for example, situated in the immediate vicinity of a coupling range between the resonator and the waveguide, also the coupling between ring resonator and waveguide can be influenced alternatively or additionally.

The control unit 8 is further connected to the detector unit 7 via connection 85. The connection 85 transmits data regarding the modulation frequencies or signals mirroring the modulation signals to detector unit 7.

As mentioned above, each of the optical resonators 41-44 in the specific embodiment of FIG. 1 has a different optical length in a base state. In order to use the sensor arrangement for measuring an observable over an extended range, each of the optical resonators is covered by a material that allows the selective accretion of the substance to be detected by said ring resonator. The active layer may be a coating which specifically targets specific biological substances or groups of substances or specific chemical substances or compounds. While each of the optical resonators may include a coating of a material for selectively accreting a substance, the optical resonators can be configured for detecting, for example, changes in temperature or changes in pressure in different embodiments. While in the example of FIG. 1 each of the optical resonators 42-44 includes an active layer. Since optical resonator 41 is not covered by an active layer, none of the substance to be detected may dock to the resonator. Optical resonator 41 is therefore configured to not detect the observable. In some embodiments, as will be discussed later, optical resonator 41 may be encapsulated so that it is not exposed to the substances to be detected or to the observables to be detected. Said encapsulated resonator may be used as a gauge resonator.

The optical resonance circuit 4 is mounted on a substrate and has a casing 45. Additionally, circuit 4 includes interfaces 46 through 48. Interface 46 allows light generation circuit 2 to be coupled to waveguide 5, which is an integral part of the optical resonance circuit 4, while interface 47 allows detector unit 7 to be coupled to waveguide 6, which is an integral part of the optical resonance circuit 4. The interfaces are optical couplers, for example, including an interface for an optical fiber (or several optical fibers) of the light generation circuit feeding light to waveguide 5 or for a optical fiber (or several optical fibers) receiving light from waveguide 6. Interface 48 is a signaling interface, which may transmit control signals to modulators 81-84. In some embodiments, the signals may also include the modulation signal itself. The signals are forwarded by e.g. wires connected to the optical resonance circuit 4. By supplying the optical resonance circuit 4 with interfaces and/or a casing, said circuit can be coupled and removed from the other components of the optical sensor arrangement 1. The optical resonance circuit is then its own optical sensor arrangement or component, which can be disposed of after performing a measurement.

The portions of the optical resonators 42-44 which are covered by the active layer are different in size. This is represented by the active layer 92 covering a quarter of the surface of optical resonator 42, by active layer 93 covering half of the surface of optical resonator 42 and by active layer 94 covering three quarters of the surface of optical resonator 44. If the resonators are substantially equal in their length, and the active material of the active layers 92-94 has the same concentration in each of those layers, then the resonance frequencies of each of the optical resonators 42-44 will be shifted differently. If the optical resonance circuit 4 is exposed to a fluid containing a substance to be detected and the shift of the resonance frequencies has an approximately linear relationship with the quantity of the substance accrued to the active layer, then the shift of resonance frequencies of optical resonator 44 will be about three times as large as for optical resonator 42. If the shift of optical resonator 44 is about the interval of the FSR and the optical resonator therefore saturated, optical resonator 42 will still give a meaningful result. On the other hand, if only very little of the substance accrues to the active layer, while the shift of resonance frequencies of optical resonator 42 might be almost negligible, the shift of resonance frequencies of optical resonator 44 may be large enough to be measured.

This shall be further explained with reference to FIG. 1b. The three diagrams illustrate the effect of the presence of the observable on the transmission spectrum of each of resonators 42-44. The transmission spectrum of optical resonator 41 is assumed to not be affected by the presence of the observable. In FIG. 1b, FSR indicates the free spectral range of each of the optical resonators, A indicates the wavelength incident on optical resonator x, $\Delta\lambda_x$ indicates the shift of resonance frequencies due to the active material 96 accruing the substance 97 to be detected. The dotted transmission resonance peaks correspond to the base state of each optical resonator while the solid transmission resonance peaks illustrate the shifted transmission resonance peaks. It is evident that shift $\Delta\lambda_{44}$ is in the range of the FSR and optical resonator 44 is in an almost saturated state. However, the shifts $\Delta\lambda_{42}$ and $\Delta\lambda_{43}$ are smaller and can be identified. If the concentration of the substance 97 was lower, the most sensitive resonator 44 would still show a shift even if the less sensitive resonators 42 and 43 show no measurable shift.

Figure 5:
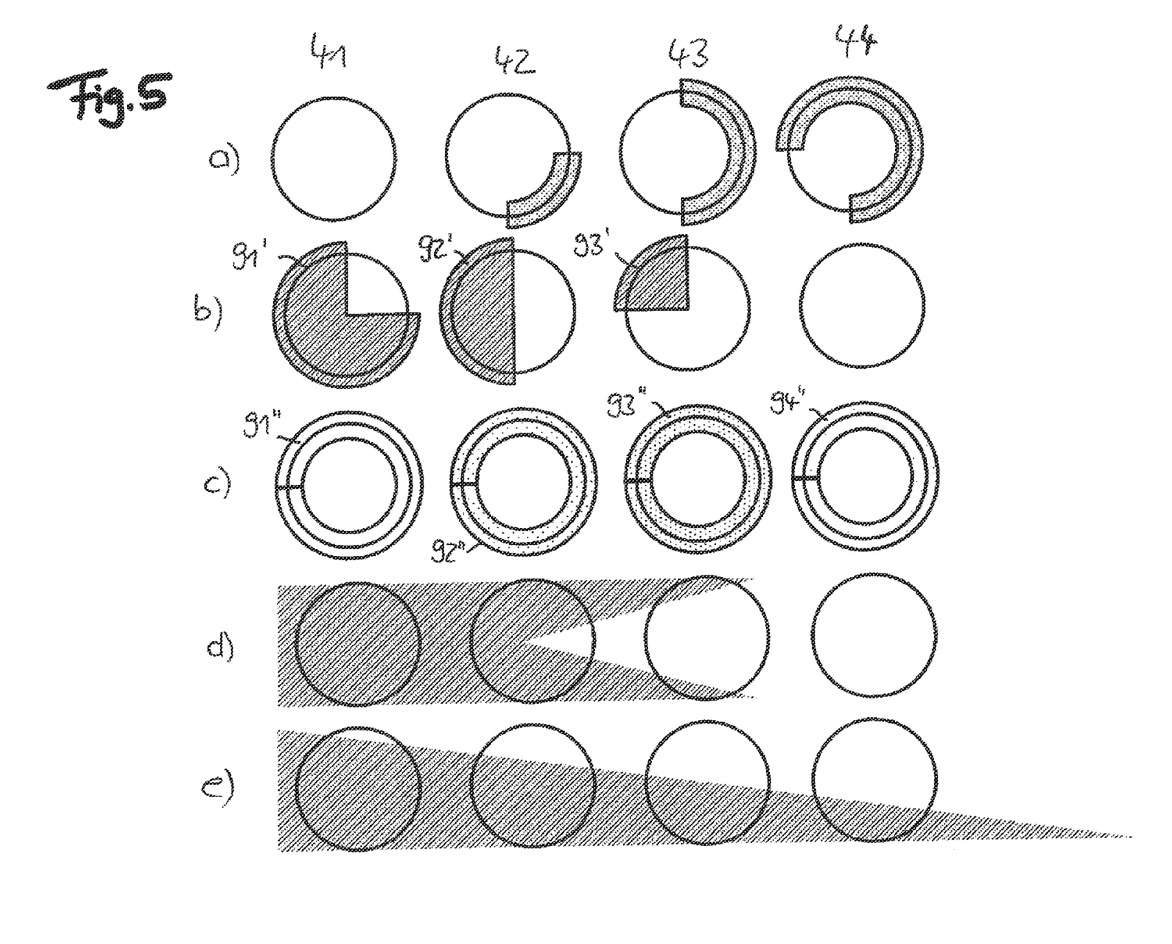
FIGS. 5a through 5e illustrate various examples of resonator arrays, according to embodiments of the disclosure.
Figure 6:
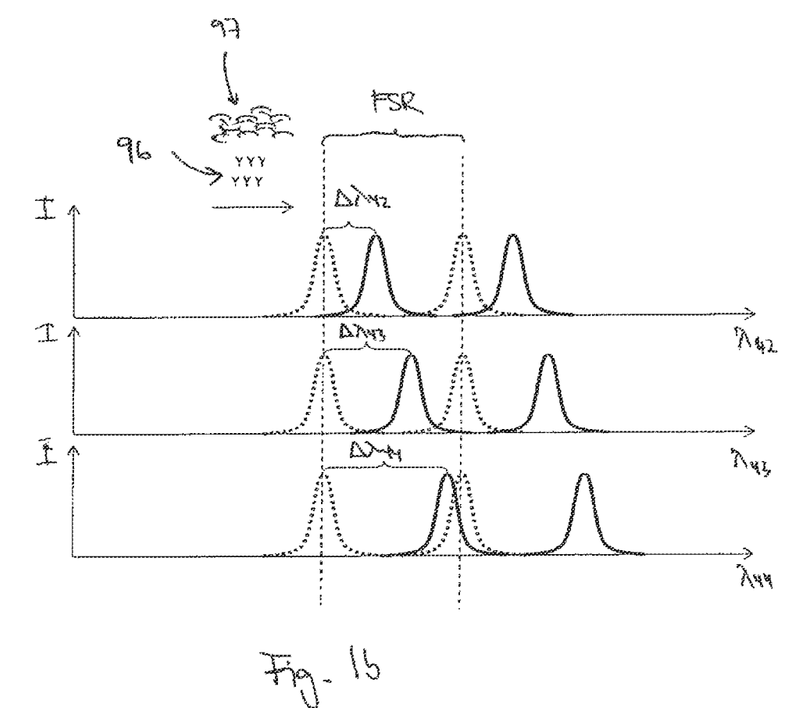

In the example of FIG. 1, the subject matter is explained with reference to the active material of the active layers having an equal concentration in each active layer, but the size of the portion of the resonator to which the active layer is applied being different. Obviously, different embodiments can cover an equal portion of the optical resonator, but including an active layer which has a differing concentration of the active material. Various other examples are explained in connection with FIG. 5.

An option for coupling the waveguides and each of the optical resonators is to use a Mach-Zehnder interferometer.

The waveguides are further configured such that they are a polarization-maintaining single mode waveguide. However, different waveguides carrying not only a TE or TM mode can be employed.

Figure 2:
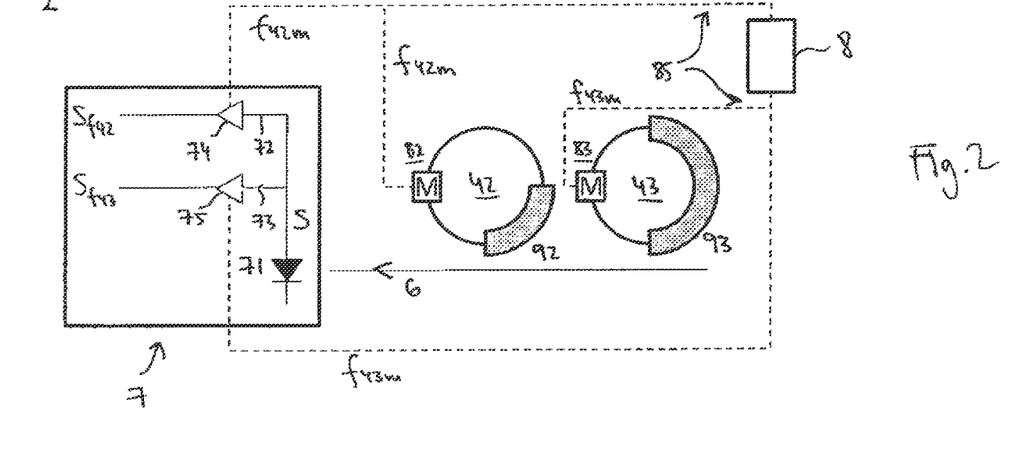
FIG. 2 shows a more detailed view of a detector unit and control unit coupled to the optical resonance circuit, according to embodiments of the disclosure.

FIG. 2 discloses a subunit of the optical arrangement 1 illustrating how the signals passing through different optical resonators may be identified in the detector unit. In FIG. 2 only the optical resonators 42 and 43 are shown. Each optical resonator may be affected by modulation devices 82 and 83, which are devices for modulating an electrical field. The detector unit 8 includes a microcontroller for controlling the modulation frequencies. Since the control unit is an electronic unit, the modulation frequencies are much lower than the frequencies of the light traveling in the optical resonators, i.e., the modulation frequencies and the frequencies of the light passing therethrough may be different by several orders of magnitude.

In the following, it is assumed that light generated by the light generation circuit is such that during a time interval at least one wavelength of the emitted light, the first light component, has a frequency of $f_{42}$ corresponding to a resonance frequency of optical resonator 42. Furthermore, the second light component has a wavelength corresponding to a frequency $f_{43}$, which is a resonance frequency of optical resonator 43. The frequencies $f_{42}$ and $f_{43}$ may be different from each other.

The control unit 8 is configured to modulate the optical length of the first and second resonators by a modulation frequency $f_{42m}$ for the first optical resonator and $f_{43m}$ for the second optical resonator. The control unit also forwards the signal carrying the modulation frequencies $f_{42m}$ and $f_{43m}$, respectively, through the connection 85 to the detector unit 7. Light traveling in the optical resonators is decoupled from the optical resonators via the drop ports 62 and 63 and travels along the optical waveguide 6 to the photosensitive element 71 of the detector unit 7. The photosensitive element 71 detects a signal S which is forwarded to connections 72 and 73. Connection 72 is the "in" port for an amplifier 74. The amplifier 74 is also fed with a signal of the modulation frequency $f_{42m}$ as a reference signal. The resulting signal is signal $S_{f42}$ since frequencies other than a signal modulated by the frequency $f_{42m}$ are canceled in the amplifier 74. Hence, signal $S_{f42}$ corresponds to a signal which is due to light entering and exiting the first optical resonator 42. Correspondingly, connection 73 enters an amplifier 75 which as a reference also receives a signal carrying the modulation frequency $f_{43m}$, resulting in a signal $S_{f43}$ which represents light passing the second optical resonator.

If the spectral content of signals $S_{f42}$ and $S_{f43}$ changes from the base state of the arrangement to the active state of the arrangement, it can be assumed that the substance which specifically docks to active layers 92 and 93 is present. The different size of the portions covered by active layers 92 and 93 illustrates the different sensitivities of the optical resonators. Since the frequency of the light traveling through the arrangement can be identified, a shift in resonance frequencies due to the presence of the observable can be determined over a broader range due to the increased sensitivity of the resonator array comprising at least resonators 41-44.

In order to exclude that changes in the optical lengths of the optical resonators are due to external circumstances and not due to the observable to be detected, gauge optical resonator 41 can be used, which is configured to not detect the observable to be detected.

Even though the amplifiers 74 and 75 are shown as part of the detector unit 7, they can also be included in the control unit 8. The signals $S_{f42}$ and $S_{f43}$ may be configured to be further analyzed by either the control unit 8 or an external data processing machine, such as a computer.

Embodiments shown in FIG. 1a include a single optical waveguide for, both, delivering the light to the optical resonator and forwarding the light from the optical resonators to the detector unit. While this has the advantage of a simple construction, it has the disadvantage that, if all resonators in their base state have a similar resonance frequency, incident light of said resonant frequency is absorbed mostly by the first optical resonator it passes (here: resonator 41), leaving little light intensity for resonators 42-44. In some embodiments, the construction is such that light traveling to and from each optical resonator is guided by individual optical paths.

Figure 3:
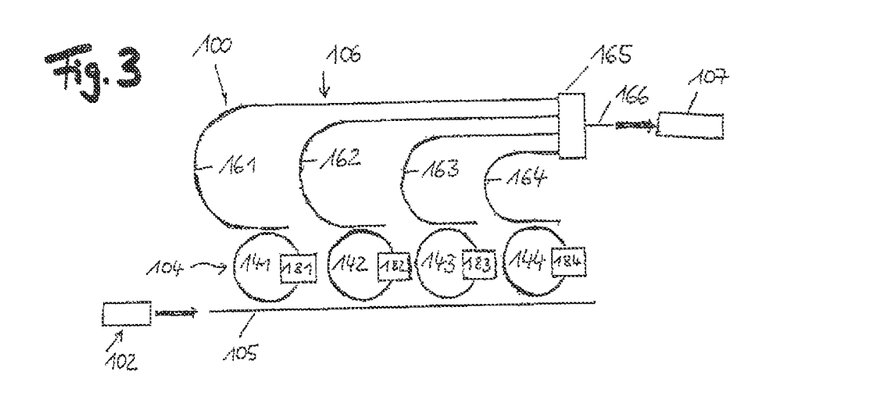
FIG. 3 an optical sensor arrangement, according to embodiments of the disclosure.
Figure 4:
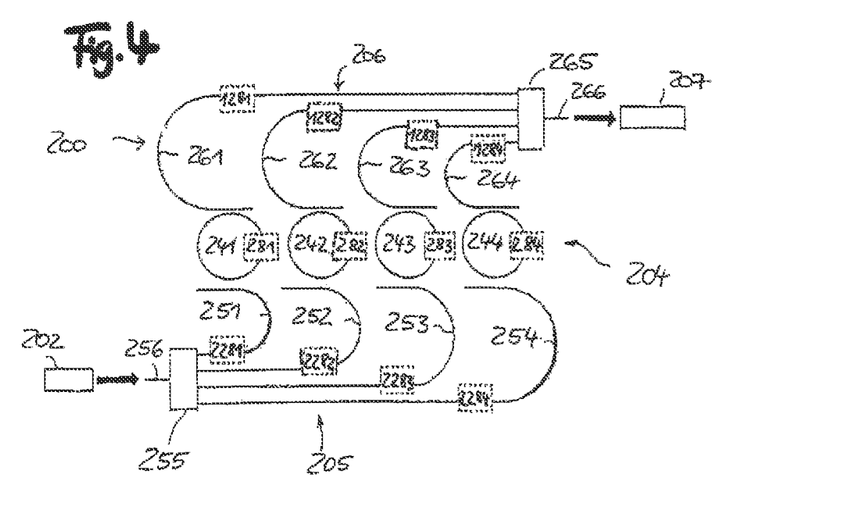
FIG. 4 an optical sensor arrangement, according to embodiments of the disclosure.

FIGS. 3 and 4 illustrate different examples of an optical sensor arrangement including individual optical paths in the form of individual optical waveguides forwarding light from an optical resonator to the detector unit.

The optical sensor arrangements 100 and 200 of FIGS. 3 and 4 include components similar to the components described in the description of FIG. 1a. Embodiments found in FIGS. 3 and 4 signify components to be similar to the components of optical sensor arrangement 1 by simply adding 100 or 200, respectively, to the respective component shown in FIG. 1a. For example, the optical resonance circuit 4 of the embodiment of FIG. 1a can be identified with optical resonance circuit 104 in the optical sensor arrangement 100 or with optical resonance circuit 204 in the optical sensor arrangement 200. If components of the following embodiments are designed differently, it will be mentioned specifically.

Optical sensor arrangement 100 includes a light generation circuit 102 and a single optical waveguide 105 which couples to an optical resonance circuit 104 through entry ports 151-154. The optical resonance circuit 104 includes four optical resonators 141-144. Optical resonator 141 is used as a gauge resonator and is encapsulated from the environment and is thus not exposed to any of the observables for whose detection the optical resonators 142-144 are specifically designed. For reasons of simplicity, embodiments of FIG. 3 do not show the portions exposed to the observable or the active layers of the optical resonators.

Each of the optical resonators 142-144 is a microring resonator coated with a specific active layer for selectively accreting a group of substances. Each active layer includes active material of an equal concentration but covers a different portion of the surface of the optical resonator, thereby increasing the range over which a measurement may be sensibly performed. The optical lengths of the optical resonators 141-144 are different such that the intensities of the light being generated by the light generation circuit 102 in the respective resonance frequency of each optical resonators are almost identical, however the FSR of each optical resonator is substantially the same.

The optical resonators 141-144 include a drop port for decoupling from the optical resonators 141-144 into their respective optical waveguides 161-164, respectively. The individual waveguides 161-164 lead to an optical coupler 165 such as a 3db or 10db coupler and are continued as a single optical path 166 to detector unit 107. The coupler 165 is an interface between the optical resonance circuit 104 and the detector unit 107. Choosing individual optical waveguides is an arrangement which is more complex but which has a higher sensitivity since light exiting any one optical resonator can be of the same frequency as light exiting another optical resonator and the intensity of the signal in each waveguide can be almost equal. As described in connection with the embodiment of FIG. 1a, each of the optical resonators 141-144 may be modulated by a modulation device 181-184 coupled to a control unit, which in this embodiment is part of the detector unit 107.

Optical sensor arrangement 200 of FIG. 4 includes a light generation circuit 202 and several optical waveguides to guide light to the optical resonance circuit 204. Light emitted from the light generation circuit 202 enters an optical waveguide 256 and a decoupler 255 (in some embodiments defining an interface between the light generation circuit and the optical resonance circuit) where the emitted light is fed into the four different optical waveguides 251-254. Each waveguide is configured such it couples to the respective optical resonators 241-244. Light exiting the optical resonators may enter individual waveguides 261-264 coupled by a coupler 265 (in some embodiments defining an interface between the detector/control unit and the optical resonance circuit) and led by a single optical waveguide 266 to the detector unit 207. In some embodiments, the optical waveguide structure 205 and the optical waveguide structure 206 both include a plurality of individual waveguides, the number of waveguides corresponding to the number of optical resonators used. However, it is also possible to only use, for example, individual waveguides for two of the four optical resonators and to supply light to the remaining optical resonators by a single optical waveguide.

As illustrated by the dotted lines in FIG. 4, a modulation device coupled to a control unit may be placed so as to influence the optical length of the resonator (for example, device 281 in the first optical resonator 241), the optical waveguide leading to the first optical resonator 241 or the waveguide 261 leading to the detector unit. While in the present example in connection with the first optical resonator three modulation devices 281, 1281, and 2281 are shown, in practice only one of those three devices will be realized. Whether the modulation device is for modulating the frequency or optical length of the entire optical path from the optical decoupler 255 to the optical coupler 265, or whether only the amplitude of the light is modulated or switched can be chosen based on the chosen embodiment of the optical sensor arrangement. The remaining optical resonators 242 and 244 and their respective optical path from the first decoupler 255 to the coupler 265 may be configured as described in connection with the first optical resonator 241. However, the four different optical paths shown in the optical sensor arrangement 200 may use modulation devices in different areas. For example, modulation device 1281 of the first optical path is an amplitude modulation device, the modulation device employed in the arrangement for the second optical path is a modulation device of the second optical resonator 242, while the third modulation device employed in the optical path of the third optical resonator 243 is a light chopper (or alternatively an electro-optical amplitude modulator) in the form of the modulation device 2283. In other words, usually only one modulation device for an optical path including an optical resonator is used.

In some embodiments, e.g. shown in FIGS. 3 and 4, the coupler 165 or 265 may be omitted. Instead, several photosensitive elements can be used, each photosensitive element capturing the light emitted from a single waveguide. Alternatively, a camera may be used allowing for local separation (spatial separation instead of ar in addition to time/frequency separation in multiplexing) of signals coming from each waveguide and assigning each separate signal to a particular resonator. When a camera or several photosensitive elements are use, the need for means for modulation, or a control unit configured to selectively modulate the signals is not necessary, since the different waveguides located at each waveguide coupled to the drop port of each resonator only carries the signal stemming from said resonator and the several waveguides or the camera can be used for separating the signals. All embodiments using individual waveguides for each resonator at their respective drop port can be designed this way and the means for modulation may be omitted.

Some embodiments based on the embodiments of FIG. 4 may include an optical detector unit at each of the open ends of the waveguides 251-254, measuring an absorption spectrum of light having passed the resonators. The detectors may be used as a redundant measure for detecting the observables. Alternatively, the detector unit 207 may be omitted and only the detector units at the open ends of the waveguides 251-254 be used. In some embodiments, the entire transmission spectrum measurement can be omitted, leaving a single light source, a plurality of optical paths and associated resonators, the open ends of the optical paths coupled to a detector unit. The detector units may also be replaced by a single or several cameras allowing for spatial separation of the signals from the separate waveguides.

Even though the embodiments discussed so far have been explained in the context of optical ring resonators, other resonators such as Fabry-Perot resonators may be employed.

In FIGS. 5a-5e, embodiments of optical resonator arrays are shown. While all embodiments include four resonators, this is merely an example and more (or less) resonators may be employed. Each row of FIG. 5 corresponds to a different embodiment, and each column corresponds to the configuration of the optical resonators 41-44.

The embodiments shown in FIG. 5a correspond to the embodiments of a resonator array as shown in FIG. 1a. While resonator 41 does not include an active layer (and is thus insensitive to several substances), each of the resonators 42-44 includes an active layer covering a different portion of the surface of the respective resonator.

FIG. 5b shows different portions of resonators 41-43 covered by an encapsulating layer 91'-93'. The encapsulating layer prevents any substance other from the material of the encapsulating layer to come into contact with the encapsulated portions of the resonators. Since the portions available for the detection of a substance differ over resonators 41-44 of FIG. 5b, the induced shifts by a substance which can alter the effective refractive index without a specific active layer are different as well (because to material of the microring resonator is specific to the observable, for example). The shift induced in resonator 44 is largest, while the shift induced in resonator 41 is smallest.

In FIG. 5c, resonator 41 acts as a gauge resonator and its surface is entirely covered by an encapsulating layer 91". The surfaces of resonators 42-44 of FIG. 5c are each entirely covered by an active layer 92"-94". Each active layer includes an active material. The concentration of the active material of the active layers 92"-94" varies tough: The concentration of the active material of active layer 92" is lower than the concentration of the active material of active layer 93" and concentration of the active material of active layer 94". The differing concentrations are indicated by the different densities of dots of the pattern filling each of the representations of active layers 92"-94".

Embodiments of FIGS. 5a and 5c can also be combined. If a resonator array included, for example 9 resonators, where 2 resonators have a portion of their surface covered as shown for resonator 42 in FIG. 5a, 2 resonators have a portion of their surface covered as shown for resonator 43 in FIG. 5a, 2 resonators have a portion of their surface covered as shown for resonator 44 in FIGS. 5a and 2 further resonators are entirely covered with an active layer (not shown in FIG. 5a), and a first of each of the two resonators having an active layer covering the same portion has a concentration of an active material different from the second resonator having an active layer across an equally large portion, then the range of substance concentrations through which the arrangement can measure reliably is greatly enhanced.

FIG. 5d shows a resonator array including a single encapsulating layer 95. The geometry of the encapsulating layer is chosen so that different portions of resonators 41-44 are covered by the encapsulating layer. The embodiment is similar to the embodiment shown in FIG. 5b.

FIG. 5e shows a single active layer 96 which covers different portions of each of the resonators 41-44 resulting in an embodiment similar to the embodiment shown in FIG. 5a.

Various modifications and additions can be made to the exemplary embodiments discussed without departing from the scope of the disclosure. For example, while the embodiments described above refer to particular features, the scope of this disclosure also includes embodiments having different combinations of features and embodiments that do not include all of the described features. Accordingly, the scope of the disclosure is intended to embrace all such alternatives, modifications, and variations as fall within the scope of the claims, together with all equivalents thereof.

The invention claimed is:

1. An optical sensor arrangement for measuring an observable, the arrangement comprising:

an optical resonance circuit including at least a first, a second, and a further optical resonator, each of said optical resonators comprising an entry port for coupling light into the optical resonator and a drop port for decoupling light from the optical resonator, the entry port being different than the drop port;

wherein the first and second resonator are partially covered by an encapsulating layer and are configured such that only a non-zero portion of the first and second resonator detects the presence of the observable, the non-zero portion not being covered by the encapsulating layer, a size of the portion of the first resonator being different from a size of the portion of the second resonator and wherein the further resonator is configured such that it is not exposed to the observable, wherein each portion of the first and second resonator configured to detect the observable comprises an active layer of the same material for the selective accretion of one or more substances to be detected;

the optical resonance circuit further configured to be coupled to a light generation circuit; and the optical resonance circuit further configured to be coupled to a detector unit for detecting light.

2. The optical sensor arrangement of claim 1, wherein a concentration of an active material of the active layer of the first resonator is substantially equal to a concentration of an active material of the active layer of the second resonator.

3. The optical sensor arrangement of claim 1, wherein the optical resonance circuit includes further resonators, each of those further resonators configured such that only a portion of each resonator is exposable to the observable, a size of the portion of each of the resonators being different from the size of the portion of the first and second resonator.

4. An optical sensor arrangement for measuring an observable, the arrangement comprising:

an optical resonance circuit including at least a first, a second, and a further optical resonator, wherein the further resonator is fully encapsulated by an encapsulating layer, each of said optical resonators comprising an entry port for coupling light into the optical resonator and a drop port for decoupling light from the optical resonator, the entry port being different than the drop port;

wherein the first and the second resonator are partially covered by an encapsulating layer, and each comprise an active layer for the selective accretion of one or more substances to be detected, where a non-zero concentration of an active material of the active layer in the first and second active areas is different and the active material is the same and wherein the further resonator is configured such that it is not exposed to the observable;

the optical resonance circuit further configured to be coupled to a light generation circuit; and the optical resonance circuit further configured to be coupled to a detector unit for detecting light.

5. The optical sensor arrangement of claim 4, wherein the optical resonance circuit includes at least one further resonator not including an active layer.

6. The optical sensor arrangement of claim 4, wherein in a base state of the optical resonance circuit an optical length of the first resonator is substantially equal to an optical length of the second resonator.

7. The optical sensor arrangement of claim 4, the arrangement further comprising a control unit configured to selectively modulate at least one of the following:

an optical length of the first or second resonator, an amplitude of the first light component or an amplitude of the second light component.

8. The optical sensor arrangement of claim 4, wherein the detector unit is part of the arrangement and is optically coupled to the drop port of each of the at least two optical resonators.

9. The optical sensor arrangement of claim 4, wherein the detector unit is part of the arrangement and includes an amplifier, preferably a differential amplifier for evaluating output signals of the at least one light sensitive element.

10. The optical sensor arrangement of claim 4, wherein the light generation circuit is part of the arrangement and is coupled to the first and second optical resonator by a single optical waveguide or wherein the first optical resonator is coupled to the light generation circuit by a first optical waveguide and the second optical resonator is coupled to the light generation circuit by a second optical waveguide.

11. The optical sensor arrangement of claim 4, wherein the detector unit is part of the arrangement and is coupled to the first and second optical resonator by a single optical waveguide or wherein the first optical resonator is coupled to the detector unit by a third optical waveguide and the second optical resonator is coupled to the detector unit by a fourth optical waveguide.

12. A method for detecting at least one observable by means of the optical sensor arrangement of claim 4, wherein the first and second optical resonator are brought into contact with an medium to be analysed and measuring an output signal of the at least one photosensitive element to determine whether an observable of or in the medium is detected.

13. The sensor arrangement of claim 1, wherein the further resonator is fully encapsulated by a further encapsulating layer.

14. The sensor arrangement of claim 1, wherein the encapsulating layer is a single encapsulating layer.

15. The sensor arrangement of claim 1, wherein the further resonator is also covered by the encapsulating layer.

16. The sensor arrangement of claim 1, wherein the encapsulating layer of the first resonator is spatially separated from the encapsulating layer of the second resonator.

* * * * *